United States Patent [19]

Atwood, Jr.

[11] Patent Number: 4,998,913

[45] Date of Patent: * Mar. 12, 1991

[54] ELECTRONIC STIMULATING DEVICE

[76] Inventor: John A. Atwood, Jr., 916 Perrin Dr., Arabi, La. 70032

[ * ] Notice: The portion of the term of this patent subsequent to Feb. 19, 2008 has been disclaimed.

[21] Appl. No.: 338,312

[22] Filed: Apr. 14, 1989

[51] Int. Cl.$^5$ .............................................. A61N 1/00
[52] U.S. Cl. ......................................... 600/14; 600/9; 128/422
[58] Field of Search ...................... 128/421, 422, 907; 600/9, 13, 14

[56] References Cited

U.S. PATENT DOCUMENTS

| | | | |
|---|---|---|---|
| 3,908,669 | 9/1975 | Man et al. | 128/422 |
| 3,920,025 | 11/1975 | Stasz et al. | 128/423 R |
| 4,121,594 | 10/1978 | Miller | 128/422 |
| 4,124,030 | 11/1978 | Roberts | 128/422 |
| 4,233,986 | 11/1980 | Tannenbaum | 128/421 |

FOREIGN PATENT DOCUMENTS 2143131 2/1985 United Kingdom .................. 600/14

Primary Examiner—Max Hindenburg
Assistant Examiner—Kennedy J. Schaetzle
Attorney, Agent, or Firm—Keaty & Keaty

[57] ABSTRACT

The invention relates to an electronic stimulating device which produces low frequency pulsating signals generated by a relaxation oscillator. The electronic circuit board is mounted within a lightweight portable housing to enable a user to conveniently carry the device at all times, if desired.

7 Claims, 4 Drawing Sheets

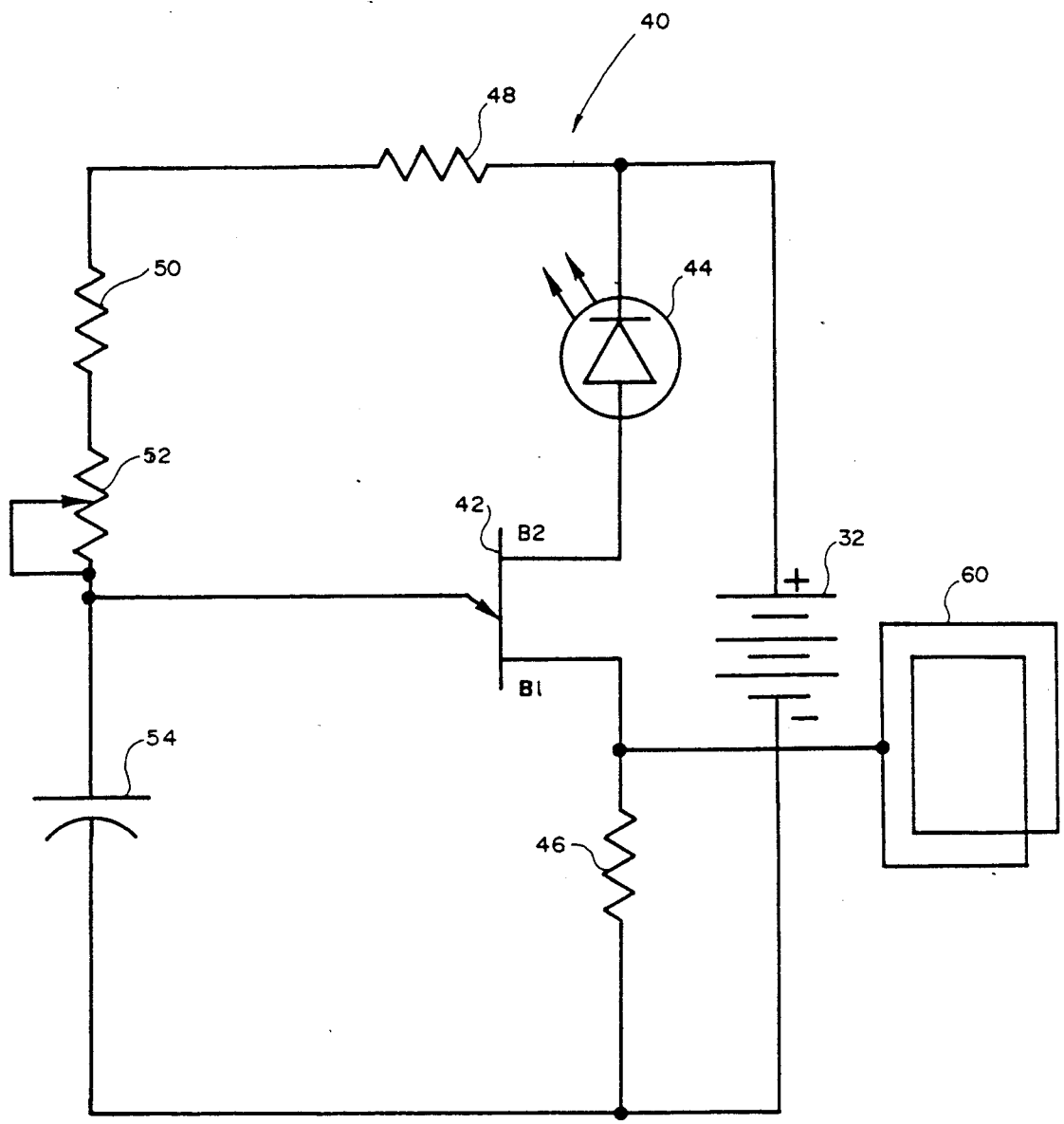
F I G. 3

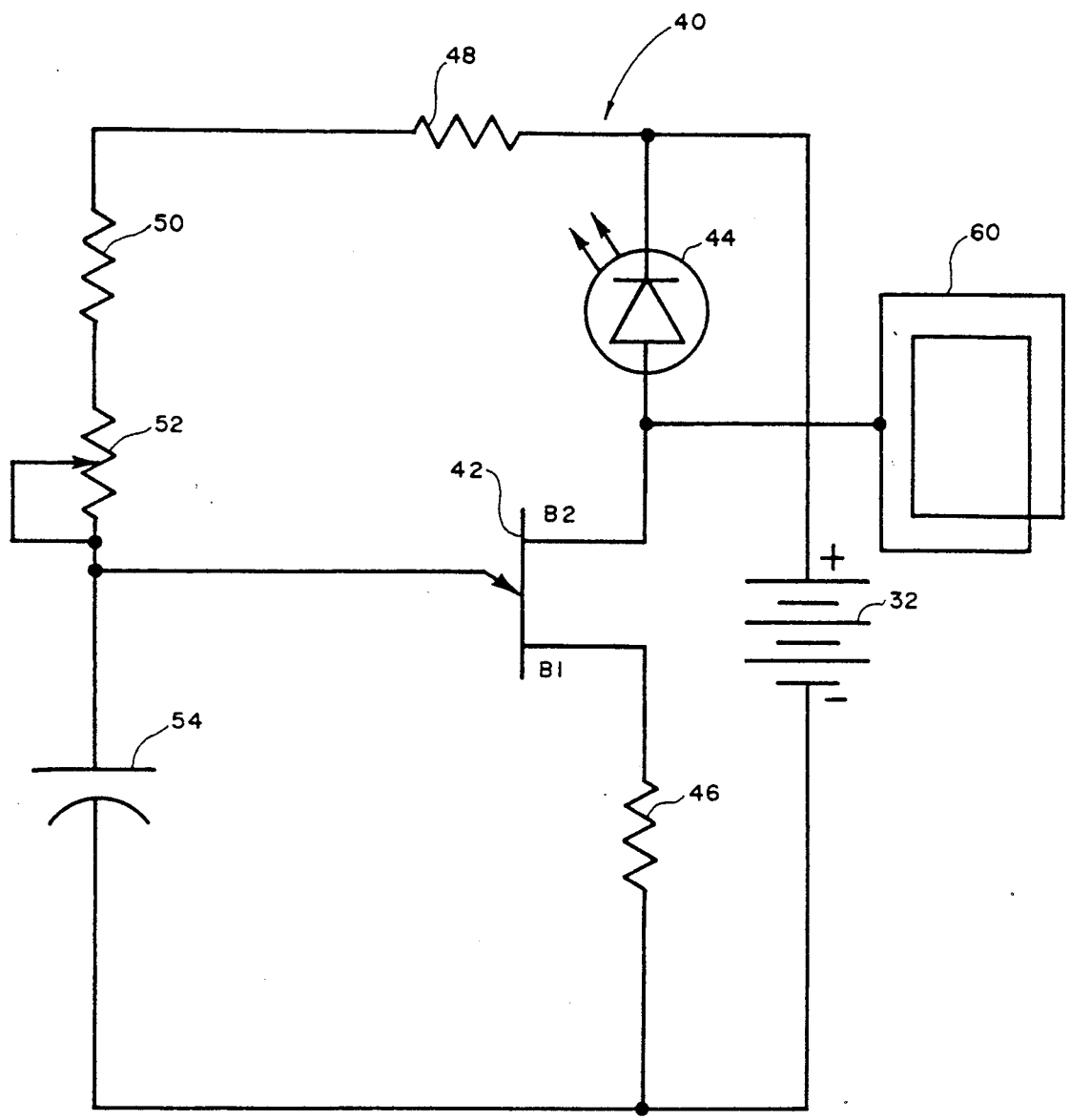
F I G . 4

ELECTRONIC STIMULATING DEVICE

BACKGROUND OF THE INVENTION

The present invention relates to a new and improved electrotherapeutic device. More specifically, the present invention relates to devices which utilize electrically generated pulses for balancing biological energy which moves to and from intestinal organs.

Acupuncture is an Oriental treatment which utilizes special needles, which are inserted into muscular tissues for treatment of various nerve-associated symptoms, such as for example, neuralgia pains.

There is also known a thermal acupuncture method which is called moxibustion which requires heating of the acupoints with a smoldering herb.

Still, there exists another method, acupressure, which provides for application of pressure by fingers of acupuncture points in order to stimulate or relax the organs. All of these methods are designed to achieve one purpose—to balance movement of bioenergy to and from the vital organs along pathways (meridians) which interconnect the organs and glands to form a network.

In the traditional Oriental viewpoint, the main reason for organ-related malfunctions in a body is an inharmonious (or imbalanced flow) of bioenergy from organ to organ.

The modern science has developed various methods and complicated equipment for testing and evaluating energy balance in a human body.

Kinesiology sets as its purpose the study of the principles of mechanics and anatomy in relation to human movement. Modern testing devices allow testing of bioenergy of a human body, which is part of the study conducted by kinesiology experts.

The theory of energy healing, on which acupuncture or acupressure methods are based, teaches that in order to cure undesirable symptoms one has to stimulate the acupoints, thus balancing the flow of bioenergy in a human body. The acupoints have generally increased electrical potential which is measurable with today's sophisticated electronics. The acupoints are located along the meridians of energy.

The present invention concerns itself with an electronic device which is designed to balance a flow of bioenergy, thereby stimulating or relaxing the organs to provide therapeutic treatment to a person, suffering from symptoms of, for example, minor neurological discomfort.

It is, therefore, an object of the present invention to provide an electronic stimulating device designed to balance a flow of bioenergy for stimulation or relaxation of a human body.

It is a further object of the present invention to provide a lightweight portable electronic device which is inexpensive and easy to manufacture.

It is still a further object of the present invention to provide an electronic device which creates a pulsating electro-magnetic field of low frequency.

These and other objects of the invention will be more apparent from the following description of the invention.

SUMMARY OF THE INVENTION

The present invention achieves its objects in a simple and straightforward manner. The electronic stimulating device in accordance with the present invention has a lightweight portable housing which houses a relaxation oscillator circuit and a battery for energizing the circuit. The low frequency pulsating signals are generated by the relaxation oscillator, the waveform of the oscillator generated pulses can be sawtooth, positive square or negative square waveforms.

The device for producing the various waveforms provides for the use of a relaxation oscillator which utilizes a unijunction transistor, a plurality of resistors, at least one of which is a variable resistor, a capacitor for developing a voltage potential on the emitter of the unijunction transistor, with the capacitor discharging through one of the resistors in emitter and base one of the resistor.

BRIEF DESCRIPTION OF THE DRAWINGS

Reference will now be made to the accompanying drawings, in which

FIG. 3 is a schematic diagram of the relaxation oscillator of the present invention designed to generate a positive pulse waveform.

FIG. 4 is a schematic diagram of the relaxation oscillator of the present invention designed to generate a negative square waveform.

DETAILED DESCRIPTION OF THE PREFERRED EMBODIMENT

Figure 1:
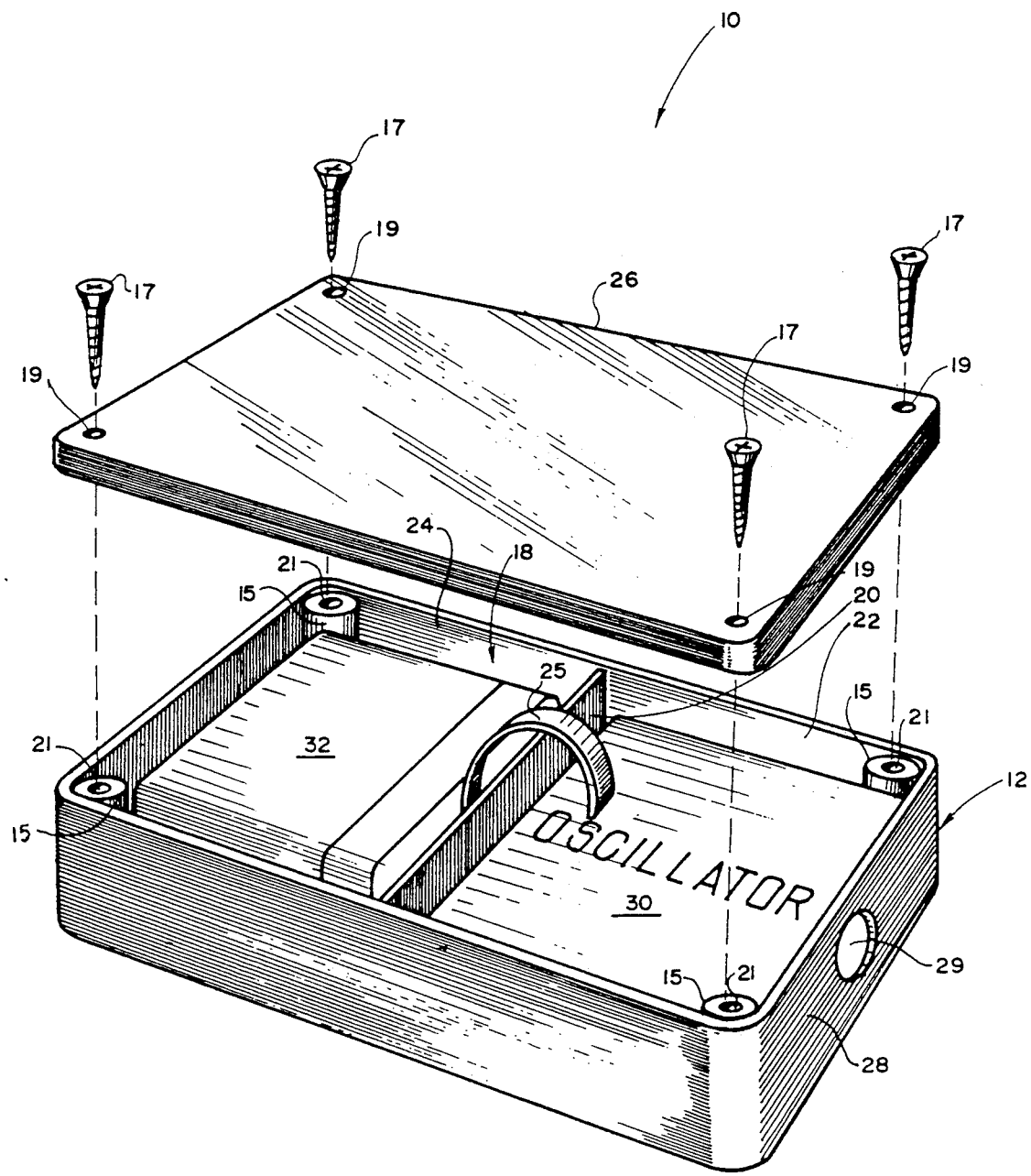
FIG. 1 is an exploded perspective view of the device according to this invention.

Referring now to the drawings and more particularly to FIG. 1, the device in accordance with the present invention is generally designated by numeral 10. The electrotherapeutic device 10 comprises a portable, lightweight housing 12 which has a closed bottom and vertically extending walls attached to the bottom to form an interior chamber 18. The chamber 18 is divided into two compartments by a separation plate 20, dividing the interior chamber into a circuit board chamber 22 and a battery, or power source chamber 24. The box 12 is shown to have a general parallelepiped configuration; however, the shape of the box can be changed if necessary.

The box 12 is provided with a cover 26, sized and shaped so as to cover the open top of the box 12, along the perimeter of its walls. The cover 26 can be bolted to the box 12 or otherwise secured thereto, so as to be detachably affixed to the box 12. In the embodiment shown in FIG. 1, the cover 26 is secured to the box 12 by four screws 17 passing through apertures 19 made in the cover 26 which are aligned with respective apertures 21 formed in supports 15 secured at four corners in the box 12.

One of the vertically extending walls of the box 12, wall 28, is provided with an opening 29 therethrough, the purpose of which will become more apparent hereinafter. Mounted within the chamber 22 is a circuit board 30 carrying the electronic circuit of a relaxation oscillator 40 in accordance with the present invention.

Mounted within chamber 24 is a power source, such as 9-volt battery 32 supplying electrical power to the electronic circuit of the relaxation oscillator 40. The battery 32 and the relaxation oscillator are disengagingly connected by wires 25 extending from chamber 24 to chamber 22.

Figure 2:
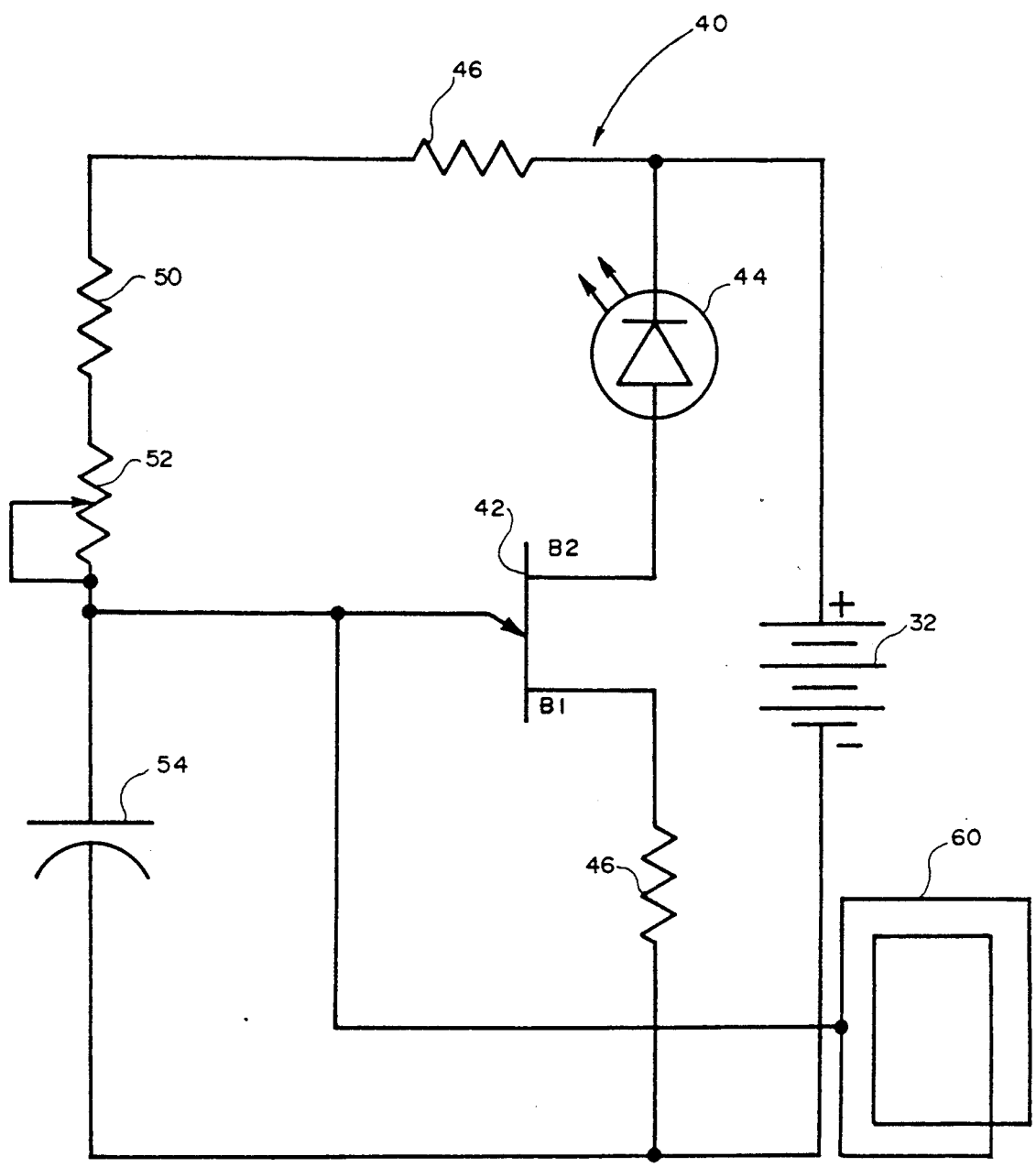
FIG. 2 is a schematic diagram of the relaxation oscillator of the present invention designed to generated sawtooth waveform.

Reference will now be made to FIGS. 2–4 illustrating some of the preferred embodiments of the electronic circuit of the relaxation oscillator in accordance with the present invention.

The relaxation oscillator illustrated in FIG. 2 is designed to produce a sawtooth waveform. A suitable electronic circuit for oscillator 40 comprises a transistor comprising emitter/base structure 42 connected to diode 44 and resistor 46. Connected to the diode 44 is a first resistor 48 and a second resistor 50. Connected in series to resistor 50 is a variable resistor 52, which in turn is connected in series to a capacitor 54.

An antenna 60 is provided to facilitate delivery of the signal generated by the relation oscillator 40 outside of the housing 12.

The light-emitting diode 44 is aligned with an aperture 29 in the wall 28 of the box 12, so that visual observation can be conducted of the operative mode of the relaxation oscillator and non-operation thereof can be visually detected which may be due to inability of the power supply to provide sufficient power to facilitate function of the electronic circuit.

The transistor 42 may be a unijunction transistor. The resistor 48 may be a 1 Kohm. Variable resistor 50 may be a 10 Kohms, set on 4.1 Kohms. The capacitor 52 may have a capacitance of 10 microfarads, while resistor 46 may have a resistance in the order of 43 Kohms.

The relaxation oscillator used in the present invention is designed to take advantage of the frequency which is determined by a capacitor-resistor combination. This oscillator has distorted wave shapes, allowing various outputs such as square waves, trapezoidal waves, traingular waves and pulses of a very short duration. The use of the unijunction transistor in the relaxation oscillator was influenced by the existence of a negative resistance region in its emitter characteric.

FIG. 2 illustrates a relaxation oscillator which produces "sawtooth" waveform. FIG. 3 illustrates a relaxation oscillator which produces positive pulse waveform and FIG. 4 illustrates a relaxation oscillator which produces negative pulse or negative square waveform.

Operation of the relaxation oscillator 40 will now be addressed in more detail.

The transistor 42 has a peak voltage Vp and a valley voltage Vv. Peak point voltage Vp controls firing of transistor 42 while valley voltage Vv controls the voltage point at which transistor 42 turns off.

The system time constant, that is the time required to transmit signals from input to output, can be determined by the value of the resistance and capacitance, in this case by resistance of resistors 48, 50, 52 and capacitor 54. The resultant time constant value RC (in seconds) determines frequency of the relaxation oscillator 40.

The timing circuit of the oscillator 40 can be modified, so that the on-off switching of the transistor 42 produces a rectangular wave at base 2 of the transistor 42.

Capacitor 54 charges through variable resistor 52, resistors 50 and 48 until it acquires a charge equal to the firing peak voltage Vp. At this point, the transistor 42 fires and the Consequently, a negative voltage spike is produced at emitter base 2 when the transistor 42 fires.

The electronic circuit 40 of the present invention generates a low frequency current of about 7–10 cycles per second.

A pulsating electro-magnetic field with the cycle frequency of 7–10 per second creates a certain magnetic signal which is believed to provide a therapeutic effect on a human body by stimulating and balancing the flow of bioenergy along acupuncture meridians.

Alternatively, a resistor 46 may be substituted by a variable resistor connected to base one of the unijunction transistor 42. Depending on the type and the kind of the transistor used, the resistance of the resistor 46 will change from one to two hundred ohms, in accordance with a particular elements utilized in the relaxation oscillator circuit.

The relaxation oscillator of the present invention can operate at frequency from the range of 7–30 Hertz. It was found that such frequency range of below 30 Hertz demonstrates a more beneficial effect on a human body than frequency range of above 30 Hertz. It can be invisioned, however, that under certain circumstances, this frequency range may be increased depending on the particular type of reaction expected by creation of a high frequency gravitional field in close proximity to a human body.

Many modifications and changes in the embodiments described herein will be apparent to those skilled in the art. I, therefore, pray that my rights to the present invention be limited only by the scope of the appended claims.

I claim:

1. An electronic stimulating device, comprising:
a relaxation oscillator circuit for producing distorted wave shapes and a power source for said circuit; said relaxation oscillator circuit comprising a light-emitting diode connected to the power source, a unijunction transistor comprising emitter/base structure connected through emitter base 1 to a resistor and through emitter base 2 to the light-emitting diode, a resistor means for controlling oscillator frequency connected in parallel to said light-emitting diode, to a capacitor; and an antenna connected between said resistor means and the capacitor to said transistor and a lightweight portable housing means for housing the relaxation oscillator circuit.

2. The device of claim 1, wherein said housing means comprise a parallelepiped-shaped housing having a closed bottom, open top, vertically extending walls and detachably securable cover means for enclosing the relaxation oscillator circuit within the housing.

3. An electronic stimulating device, comprising:
a transistor comprising an emitter/base structure;
a battery for energizing said transistor;
a lightweight portable housing means for containing an electrical circuit comprising a transistor and a battery;
a resistor means for controlling oscillator frequency;
a capacitor means for creating a voltage potential across the emitter/base of the transistor;
said capacitor means discharging through the resistor means and an emitter and base of the transistor;
a diode connected in series to said transistor; and
an antenna connected to said transistor between the resistor means and the capacitor means.

4. The device of claim 3 wherein said housing means has a wall provided with an aperture therethrough, and said diode is a light-emitting diode positioned in alignment with said aperture to allow visual determination of a charged condition of said transistor.

5. The device of claim 3 wherein said resistor means comprises at least one variable resistor.

6. The device of claim 3 wherein said transistor is a unijunction transistor.

7. An electronic stimulating device, comprising;
a lightweight portable housing means for containing an electrical circuit;
a relaxation oscillator and a battery for energizing said oscillator mounted in said housing;
said oscillator comprising a transistor comprising emitter/base structure, a resistor means for controlling oscillator frequency, a capacitor means for creating a voltage potential across an emitter of the transistor, said capacitor means discharging through the resistor means and an emitter and a base of the transistor, a diode connected in series to said transistor, and an antenna connected to a base of said transistor.

* * * * *